(12) United States Patent
Yabusaki (10) Patent No.: US 11,266,308 B2
(45) Date of Patent: Mar. 8, 2022

(54) METHOD AND DEVICE FOR EVALUATING TEAR FLUID STATE

(71) Applicant: KOWA COMPANY, LTD., Aichi (JP)

(72) Inventor: Katsumi Yabusaki, Tokyo (JP)

(73) Assignee: Kowa Company, Ltd., Aichi (JP)

(*) Notice: Subject to any disclaimer, the term of this patent is extended or adjusted under 35 U.S.C. 154(b) by 606 days.

(21) Appl. No.: 16/306,398

(22) PCT Filed: May 29, 2017

(86) PCT No.: PCT/JP2017/019840
§ 371 (c)(1),
(2) Date: Nov. 30, 2018

(87) PCT Pub. No.: WO2017/209024
PCT Pub. Date: Dec. 7, 2017

(65) Prior Publication Data
US 2020/0315446 A1   Oct. 8, 2020

(30) Foreign Application Priority Data

May 30, 2016   (JP) .............................. JP2016-107838

(51) Int. Cl.
*A61B 6/00* (2006.01)
*A61B 5/05* (2021.01)
*A61B 3/00* (2006.01)
*A61B 3/14* (2006.01)
*A61B 3/10* (2006.01)

(52) U.S. Cl.
CPC ............ *A61B 3/101* (2013.01); *A61B 3/0025* (2013.01); *A61B 3/14* (2013.01); *A61B 3/145* (2013.01)

(58) Field of Classification Search
CPC ......... A61B 5/0059; A61B 3/14; A61B 3/103; A61B 3/1125; A61B 3/024; A61B 3/032; A61B 3/18; A61B 3/1015; A61B 3/107; A61B 3/152; A61B 5/14542; A61B 5/4266; A61B 6/032; G06T 7/0012
USPC ................. 600/476, 356, 346, 425; 351/200, 351/205–206, 209–210, 221–223, 351/245–246, 208
See application file for complete search history.

(56) References Cited

U.S. PATENT DOCUMENTS

2005/0162611 A1   7/2005   Miwa
2012/0300174 A1   11/2012   Yokoi et al.

FOREIGN PATENT DOCUMENTS

| JP | H09201334 A | 8/1997 |
| JP | 2005211173 A | 8/2005 |
| JP | 2011156030 A | 8/2011 |

*Primary Examiner* — Dawayne Pinkney
(74) *Attorney, Agent, or Firm* — Verrill Dana, LLP

(57) ABSTRACT

Provided are a method and a device for evaluating a tear fluid to objectively evaluate and determine the severity of dry eye or the like. Color information is acquired in a predetermined region of a tear fluid interference fringe image, a numerical value representing a color diversity is calculated from the color information acquired, and the numerical value representing the color diversity thus calculated is used as an index for evaluating a tear fluid state.

8 Claims, 6 Drawing Sheets

METHOD AND DEVICE FOR EVALUATING TEAR FLUID STATE

FIELD

The present invention relates to a method and a device for evaluating a tear fluid state by using a color diversity of an interference fringe generated by an oil layer of a tear fluid.

BACKGROUND

An eyeball and an eyelid are protected by a tear fluid from entry of a foreign matter, drying, a damage due to friction, and the like. The tear fluid is composed of two layers, a liquid layer including water and a glycoprotein (mucin) that occupies most of the tear fluid and an oil layer covering the liquid layer. The oil layer prevents evaporation of a liquid phase by preventing the liquid phase from being in direct contact with the air. A component of the oil layer is secreted from the meibomian gland present in the eyelid. If the meibomian gland is damaged due to aging, inflammation, scratching, or the like, the oil layer is not properly formed, causing a condition of so-called dry eye. Thus, evaluating the oil layer of the tear fluid is effective in diagnosing the severity of the dry eye.

As a method for evaluating the oil layer of a tear fluid, a device and a method for diagnosing a state of the oil layer by photographing an interference fringe formed on the oil layer and categorizing the state of the oil layer into five levels of indexes (grades) by visual inspection have been proposed (Patent literature 1 and Patent literature 2). The interference fringe of the tear fluid is basically the same as that observed in a soap bubble, a thin oil film formed on a water surface, or the like. However, in the case of the tear fluid, the interference fringe is formed by interference between light reflected on the surface of the oil layer and light reflected at a boundary of a lower surface of the oil layer and the liquid layer.

If the oil layer formed on the liquid layer is stable and uniform in thickness, an image of the tear fluid appears gray in monotone without interference of light occurring (grade 1). As the thickness of the oil layer becomes thin, that is, as the condition of the dry eye progresses, the thickness of the oil layer and a length of light wavelength satisfy a condition where the interference occurs and the interference fringe begins to appear. At the beginning, the interference fringes of different gray colors appear (grade 2), however, when the thickness of the oil layer becomes uneven, the interference fringes of various colors appear (grade 3). When the thickness of the oil layer becomes further uneven, these interference fringes of various colors are jumbled and mixed (grade 4). In a severe case of the dry eye where formation of the oil layer significantly deteriorates, the image of the tear fluid appears gray as a whole without having any interference fringe, which is clearly different from the image in grade 1 in smoothness. This can be used as an index to determine grade 5.

CITATION LIST

Patent Literature

Patent Literature 1: Japanese Patent Application Laid-Open No. Hei. 9-201334
Patent Literature 2: Japanese Patent Application Laid-Open No. 2011-156030

SUMMARY

Technical Problem

However, determining the grade of the dry eye by visual inspection in this manner requires an experienced skill for achieving an accurate diagnosis. Further, even an experienced observer reveals an inconsistency in determining a diagnosis result due to prejudice or misunderstanding, and a determination result is varied from observer to observer due to individual subjectivity, which have been problems with this method. Thus, there has been desired a method in which the state of the oil layer of a tear fluid can be automatically digitized in the similar manner as the grade determination by visual inspection.

Further, although a tear fluid image can be obtained as a video image consisting of sequential images, diagnosis of the tear fluid state by visual inspection does not allow a temporal and spatial analysis, thus making it hard to dynamically analyze information included in measurement data, such as fluidity and a state change of the tear fluid.

The present invention has been made in view of the conventional problems described above and an object of the present invention is to provide a tear fluid state evaluation method and device for evaluating a tear fluid state from a color diversity of a tear fluid interference fringe image.

Solution to Problem

The tear fluid state evaluation method and device according to the present invention include the following steps or means.

(1) Color information is acquired in a predetermined region of a tear fluid interference fringe image, a numerical value representing a color diversity is calculated from the color information thus acquired, and then the numerical value representing the color diversity thus calculated is used as an index for evaluating a tear fluid state.

(2) In (1) described above, the color information is luminance of at least one or more color elements of red, green, and blue (R, G, B) possessed by a pixel and the numerical value representing the color diversity is a variation of the luminance of each of a plurality of the pixels.

(3) In (2) described above, the variation of the luminance is usually a variance of the luminance or a standard deviation of the luminance; however, it is not limited thereto. The numerical value representing the variation may be appropriately selected from any numerical values similar or statistically equivalent to the variance or the standard deviation.

(4) In (1) described above, the color information may be a hue and the numerical value representing the color diversity may be obtained, after sorting the predetermined region into predetermined sections, as a ratio between the number of the sections in which the number of elements is not empty and the number of sections in which the number of elements is empty.

(5) In (1) to (4) described above, the tear fluid interference fringe image includes a plurality of sequential frame images constituting a moving image, and the color information in the predetermined region is acquired in each of the frame images and the numerical value representing the color diversity is calculated from the color information thus acquired.

Note that the description is given of the case where the color information is represented by a luminance value (an RGB value) as described in the above (2) and the case where the color information is represented by the hue (a hue ring, etc.) as described in the above (4); however, the present invention is not limited thereto and a method for expressing the color information may be appropriately selected from various methods.

Advantageous Effects of Invention

The present invention exhibits the following advantageous effects. The state of the interference fringe of the tear fluid can be digitized by determining the color diversity in a region of the image of interest on the basis of the color information of a pixel included in such a region, and the numerical value representing the color diversity can be used as an index for evaluating the tear fluid state. This makes it possible to objectively evaluate the tear fluid state (the severity of dry eye and a site in which the tear fluid state deteriorates on the cornea) regardless of subjectivity, experience, or the like of an observer.

Further, a planar (or spatial) distribution of the tear fluid state can be evaluated by dividing the tear fluid interference fringe image into an huge number of regions and calculating the numerical value representing the color diversity in each region, or by specifying each pixel or a small group of pixels and calculating the numerical value representing the color diversity in a region surrounding each pixel or the small group of pixels. This makes it possible to easily and objectively determine a site in which the tear fluid state deteriorates on the cornea.

Further, a temporal transition of the tear fluid state can be analyzed and evaluated by retrieving and analyzing two or more frame images in the moving image. This makes it possible to evaluate the tear fluid state with a different index, such as a rate at which the tear fluid state deteriorates over time.

DESCRIPTION OF EMBODIMENTS

Embodiments of the present invention will be described below by using examples. In the present invention, color information of all or a part of pixels in an entire region of an image or at least one or more small regions arranged in the image is acquired and a diversity of the color information of at least two or more of the pixels is calculated to determine a tear fluid state on the basis of the color diversity of an interference fringe of the tear fluid shown in such a region.

<Image Acquisition>

Figure 6:
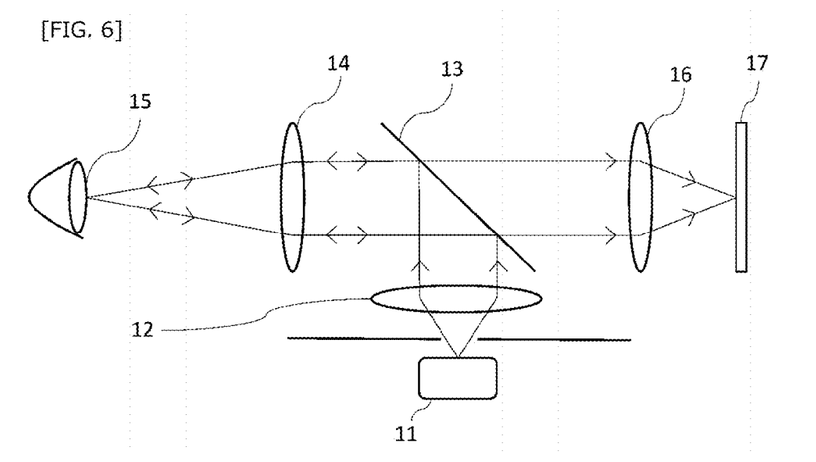
FIG. 6 is a diagram schematically illustrating a configuration of a tear fluid interference fringe image acquisition device.

As a device configured to acquire the tear fluid image on the surface of an eye (a tear fluid interference fringe image acquisition device), a conventionally known device may be appropriately used as long as it can record the photographed image showing the interference fringe of the tear fluid as digital data. For example, in the tear fluid interference fringe image acquisition device schematically shown in FIG. 6, a light beam, which is emitted from a light source 11 constituted by a white LED or the like and transmitted through a diaphragm, sequentially passes through a lens 12, a splitter 13, and an objective lens 14 and is condensed on an anterior eye portion 15 of a subject eye of a subject. Reflected light from the anterior eye portion 15 passes through the objective lens 14 and the splitter 13, so that an image is formed on an imaging element 17 via an imaging lens 16. Photographed data of the image formed on the imaging element 17 are subjected to a predetermined processing by an image processing engine and converted to image data and moving image data.

The tear fluid interference fringe image acquisition device is physically or logically connected to a tear fluid state evaluation device according to the present invention. The tear fluid state evaluation device includes a processing unit configured to compute and process data and a storing unit configured to store the image data, moving image data, and other data acquired by the tear fluid interference fringe image acquisition device. The storing unit stores a computer program and prescribed data for executing the present invention, while the processing unit processes data according to a predetermined instruction by the computer program and the like.

<Acquisition of Image Color Information>

A specific processing of the tear fluid state evaluation device will be described below. The color information is acquired from the image data of the interference fringe of the tear fluid (a tear fluid interference fringe image) obtained as described above and a diversity of the color information is calculated to obtain an index for evaluating the tear fluid state. Color elements of three colors of red, green and blue (a numerical value in the RGB color space), which is a color system used in many electronic image apparatuses, may be used as the color information. Alternatively, a numerical value in a color space using a hue by which a color can be more intuitively represented, specifically, "HSV color space" and "HLS color space", may be used.

It is generally known that a hue (H) is acquired by a conversion of the numerical value in the RGB color space as shown in the following formulas. Thus, these formulas can be used.

(In a case where Max=R)

$$H=60*(G-B)/(\text{max}-\text{min})$$

(In a case where Max=G)

$$H=(60*(B-R)/(\text{max}-\text{min}))+120$$

(In a case where Max=B)

$$H=(60*(R-G)/(\text{max}-\text{min}))+240$$

Further, as another method, the hue (H) may be acquired using a special apparatus capable of capturing an image in each wavelength. As a specific example, there is a method in which a spectroscopic filter capable of changing, gradually or stepwise, a wavelength of light passing through the filter is connected to a monochromatic camera and an image in each spectroscopic filter is acquired to obtain the hue (H).

Further, a secondary numerical value calculated from the color information may be obtained and used. Specific examples thereof may include a numerical value obtained by using the luminance of at least one or more color elements of red, green, and blue in the RGB color space as it is or a numerical value obtained by converting the luminance via a processing in a predetermined method into gray scale gradation. For example, as a method for generating a gray scale suitable for human color perception, a calculation method in which the luminance of red, green, and blue is each multiplied by a corresponding predetermined coefficient (e.g., red "0.298912", green "0.586611", blue "0.114478") and then the resulting values are summed up together is known. Such a method may be used.

Further, any of the luminance of the color elements may be used solely or two or more of the luminance may be used in combination for the calculation. For example, in a case where an average value is used, two or more of the color elements may be simply averaged to perform a calculation or each element may be multiplied by a different predetermined weighting coefficient to obtain an average value. Further, in the color space that uses the hue, for example, in the HSV color space, brightness (V) may be used as it is or after being suitably processed.

<Calculation of Color Diversity>

Examples of a method for calculating a color diversity from the color information acquired by the above-described method may include a method for calculating the number of colors included in a predetermined region (division) of the image and a method for calculating a variation of at least one or more elements of the color information acquired by the above method in the region.

First, the former method using a color space that can utilize a hue, such as the "HSV color space", will be described. A hue is divided into a predetermined number to generate sections. A hue in each pixel in the predetermined region of the image is acquired as the color information and the color information is then sorted in each section. Then, the number of elements sorted in each section is counted. In a case where the number of elements is smaller than a predetermined threshold in each section, such a section is considered to be empty, thereby counting the number of sections which are not empty. In this manner, a diversity of the color information can be evaluated.

Further, the latter method for examining the variation of at least one or more elements of the acquired color information in the region will be described. The variation is obtained by examining the color information in the RGB color space in each pixel in the predetermined region of the image and evaluating which extent an intensity of at least one or more color elements of red, green, and blue varies in the region. As the variation, a variance obtained from a value of each element may be used or a deviation value (a standard deviation or the like) calculated therefrom may be used. These values may be optionally selected and used as needed.

<Region Subjected to Calculation of Color Diversity in Image>

The diversity of the color information of the tear fluid interference fringe image thus obtained may be calculated using the entire image. Alternatively, the color diversity may be calculated in a region of each grid after optionally dividing the tear fluid interference fringe image into a grid shape.

In a case where the entire image is used or the divided region has a large area, the calculation can be performed at a low cost, thereby making it possible to instantly analyze a plurality of the tear fluid interference fringe images and display numerical values.

On the other hand, if the number of the regions divided into a grid shape is increased and a size of each region is reduced, it becomes possible to evaluate the color diversity in a further smaller region. In this case, the calculation cost increases with an increase in the number of the divided regions, thus the immediacy of the analysis is vanishing.

Further, each pixel or a pixel region in which several adjacent pixels are grouped together is defined in the image and the diversity of the color information may be obtained in pixels surrounding each pixel or in the pixel region. The diversity of the color information thus obtained has further higher resolution than the aforementioned method in which the image is divided into a grid shape. Further, such a method is advantageous in that spatial position information is completely matched with that of the original tear fluid image. On the other hand, the method requires a huge calculation cost and thus has low immediacy. Thus, the method may be preferably used for performing detailed analysis of the image and video image which have been recorded.

Note that the original tear fluid interference fringe image may be appropriately magnified or reduced for calculating the color diversity. As a magnification method, a method in which a gap of the luminance of pixel is interpolated by a function, such as a bilinear method, a bicubic method, and a Lanczos method, is preferable. As an effect of magnification, the state information that varies depending on each site can be acquired in more detail. On the other hand, as a method for reduction, any methods such as a nearest-neighbor method, a bilinear method, a bicubic method, and a Lanczos method may be used. As an effect of reduction, shortening of analysis time can be mentioned. These methods may be appropriately selected and used according to the need.

The color diversity, which is obtained from the tear fluid interference fringe image in each grid, pixel, or region such as the pixel group, may be two-dimensionally arranged, and then stored and displayed as an image that shows the tear fluid state. For creating an image, the color diversity may be expressed with a gray scale in which the luminance is increased or decreased depending on a value of the diversity. Alternatively, heat map colors obtained on the basis of the value of the diversity may be used to further facilitate the recognition of a difference in the color diversity.

Further, the color diversity of the tear fluid interference fringe image thus obtained is not only analyzed using a single image, but also analyzed in the same manner using two or more images (still images) photographed at different times or a video image (a moving image) to allow a temporal and spatial analysis of the tear fluid state. This makes it possible to noninvasively perform a dynamic analysis to determine, for example, a portion of the observation region in which the tear fluid state starts to deteriorate, the fluidity of the tear fluid, or a time point at which the tear fluid collapses. These analyses make it possible to not only perform a simple grade evaluation but also obtain detailed information on a positional relationship on the cornea, a progress, or the like of a dry eye symptom in a diagnosis of the severity of dry eye, which can be utilized for a future treatment.

Example 1

Figure 1A:
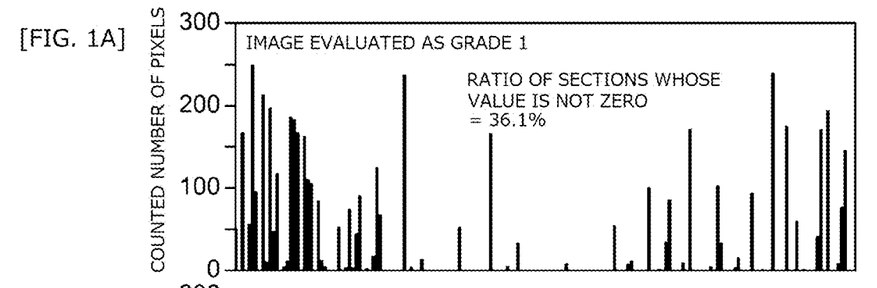
FIG. 1 is a diagram illustrating a result of evaluating a color diversity using an index indicating how many colors are included in a predetermined region.

FIGS. 1A and B show a method for evaluating a color diversity of a tear fluid interference fringe image using an HSV color space, in which an image (FIG. 1A) determined to be grade 1 by visual inspection and an image (FIG. 1B) determined to be grade 4 by visual inspection were prepared, a hue of each pixel included in a region of 320×320 pixels located at a center portion of the image was obtained as color information, the color information was examined and sorted to a section obtained by dividing a hue into 180 sections to generate a histogram, and a ratio of the sections in which the number of elements is not empty was calculated.

Figure 1B:
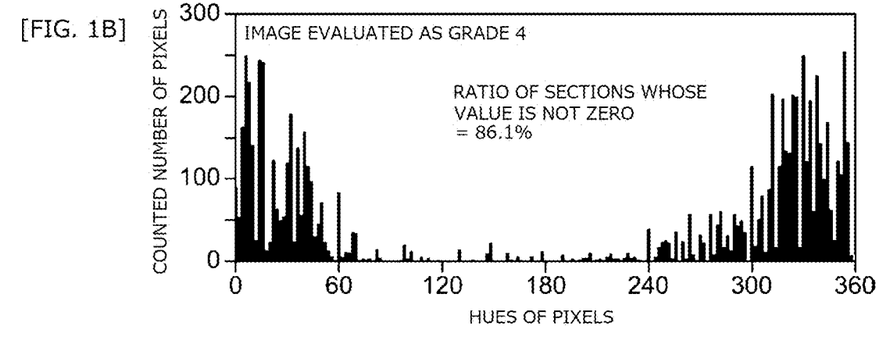

As a result, the ratio of the sections in which the number of elements was not empty was low in the image having a low grade (grade 1, FIG. 1A), while the ratio of the sections in which the number of elements was not empty was high in the image having a high grade (grade 4, FIG. 1B).

Further, Table 1 shows results in which a total of 15 images having various grades were evaluated by the same method as that described above.

TABLE 1

| IMAGE NAME | GRADE | COLOR DIVERSITY | | | |
|---|---|---|---|---|---|
| | | 180 SECTION | 360 SECTION | 180 SECTION | 360 SECTION |
| image-01 | 4 | 115 | 161 | 63.9% | 44.7% |
| image-02 | 2 | 99 | 130 | 55.0% | 36.1% |
| image-03 | 4 | 133 | 205 | 73.9% | 56.9% |
| image-04 | 2 | 75 | 91 | 41.7% | 25.3% |
| image-05 | 4 | 155 | 251 | 86.1% | 69.7% |
| image-06 | 2 | 132 | 207 | 73.3% | 57.5% |
| image-07 | 4 | 179 | 326 | 99.4% | 90.6% |
| image-08 | 1 | 65 | 79 | 36.1% | 21.9% |
| image-09 | 4 | 175 | 308 | 97.2% | 85.6% |
| image-10 | 2 | 73 | 87 | 40.6% | 24.2% |
| image-11 | 4 | 172 | 298 | 95.6% | 82.8% |
| image-12 | 2 | 105 | 146 | 58.3% | 40.6% |
| image-13 | 3 | 79 | 112 | 43.9% | 31.1% |
| image-14 | 3 | 111 | 194 | 61.7% | 53.9% |
| image-15 | 4 | 172 | 297 | 95.6% | 82.5% |

Figure 1C:
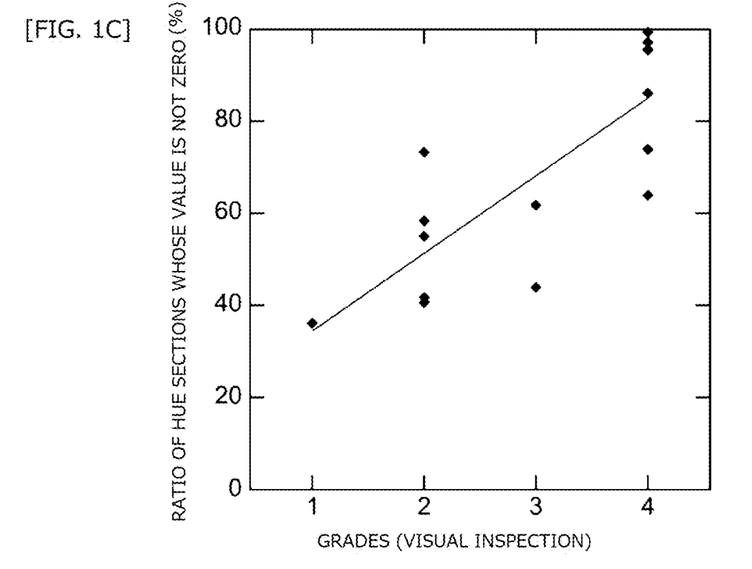

The data shown in Table 1 were graphically depicted to find the result shown in FIG. 1C. A positive correlation was observed between the grades and the ratio of sections in which the number of elements is not empty, although there were considerable variations. Specifically, it is found that the tear fluid interference fringe image determined to be grade 1 can be evaluated as having a low ratio of the sections in which the number of elements is not empty, that is, having a low color diversity, and as the grade becomes higher, the tear fluid interference fringe image can be evaluated as having a higher ratio of the sections in which the number of elements is not empty, that is, having a higher color diversity.

Example 2

Next, FIG. 2 shows an evaluation result using an RGB color space. Luminance values of red, blue, and green were obtained in each pixel included in a region of 320×320 pixels located at a center portion of the image as in Example 1 using the same image as that used in Example 1 to generate histograms. Variations in the histograms were evaluated while attention was given to a standard deviation.

Figure 2A:
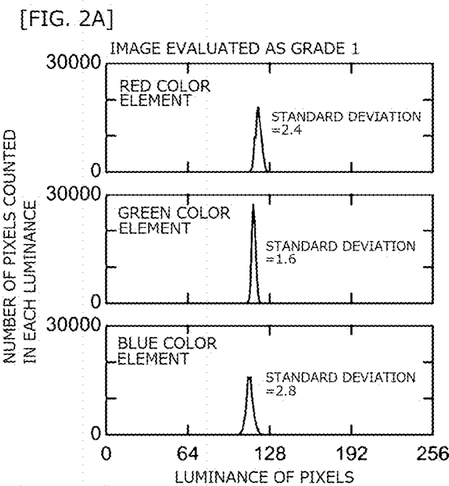
FIG. 2 is a diagram illustrating an example of obtaining the color diversity from a color variation (standard deviation) using color elements, namely, red, green, and blue, in an RGB color space.
Figure 2B:
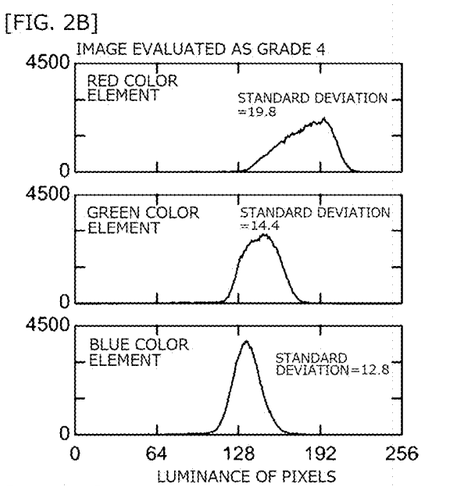

As a result, the image having a low grade showed a low standard deviation of the luminance of each RGB element in the region (FIG. 2A), while the image having a high grade showed a high standard deviation (FIG. 2B).

Table 2 shows evaluation results of a total of 15 images which were the same as those used in Example 1.

TABLE 2

| IMAGE NAME | GRADE | COLOR DIVERSITY | | | |
|---|---|---|---|---|---|
| | | Red | Green | Blue | Average |
| image-01 | 4 | 14.22 | 8.53 | 7.74 | 10.16 |
| image-02 | 2 | 4.83 | 4.52 | 5.02 | 4.79 |
| image-03 | 4 | 19.07 | 14.60 | 12.83 | 15.50 |
| image-04 | 2 | 5.86 | 5.24 | 5.41 | 5.50 |
| image-05 | 4 | 19.78 | 14.39 | 12.78 | 15.65 |
| image-06 | 2 | 6.39 | 5.58 | 6.04 | 6.00 |
| image-07 | 4 | 23.60 | 15.86 | 15.09 | 18.19 |
| image-08 | 1 | 2.42 | 1.62 | 2.80 | 2.28 |
| image-09 | 4 | 17.66 | 15.85 | 13.49 | 15.66 |
| image-10 | 2 | 3.78 | 3.39 | 4.08 | 3.75 |
| image-11 | 4 | 22.99 | 19.08 | 15.92 | 19.33 |
| image-12 | 2 | 5.54 | 4.07 | 4.13 | 4.58 |
| image-13 | 3 | 12.82 | 11.79 | 14.11 | 12.90 |
| image-14 | 3 | 9.29 | 8.81 | 11.18 | 9.76 |
| image-15 | 4 | 14.23 | 11.61 | 11.31 | 12.38 |

Figure 2C:
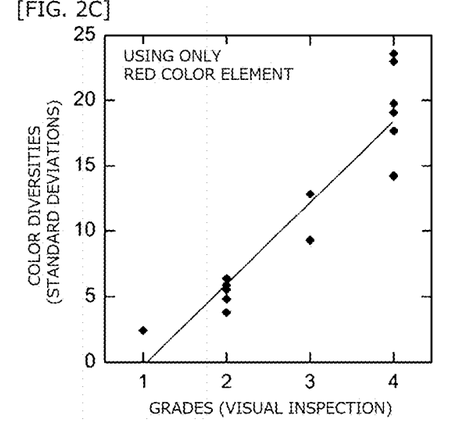
Figure 2D:
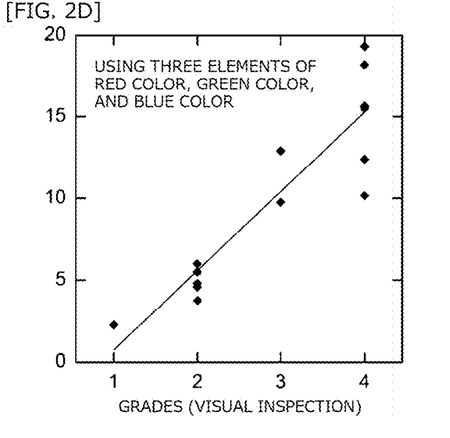
Figure 3A:
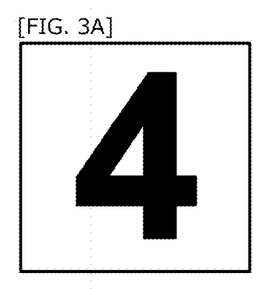
FIG. 3 is a diagram schematically illustrating how much the tear fluid state can be extracted as space information when a size of grid serving as a minimum unit for performing an image analysis is changed.
Figure 3B:
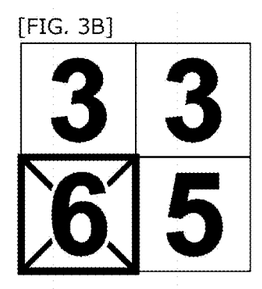
Figure 3C:
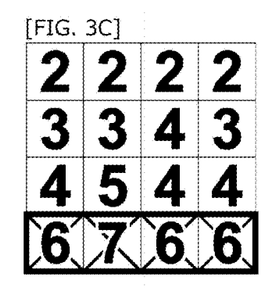
Figure 3D:
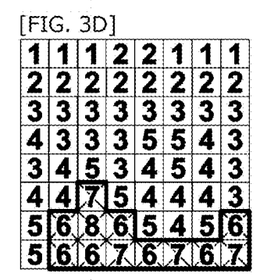
Figure 3E:
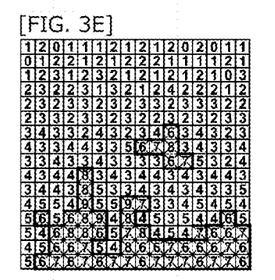

Further, FIG. 2C and FIG. 2D show results of the data shown in Table 2 in which the standard deviation of the red element and an average value of the standard deviations of 3 color elements were plotted to the grades.

As is evident from these figures, satisfactory results were obtained as high positive correlations were observed in both cases and variations were smaller than those in the method in Example 1.

From these results, it is found that the standard deviation of the color of the tear fluid interference fringe is a suitable index for evaluating the color diversity. A region having a high standard deviation of the luminance can be evaluated as having a high color diversity, while a region having a low standard deviation is evaluated as having a low color diversity. Thus, it is found that the standard deviation of the luminance is an excellent index for evaluating the color diversity of the tear fluid interference fringe image and allows digitization of the color diversity in the same manner as in the grade evaluation.

Example 3

FIG. 3 shows an example of the color diversity obtained in an entire tear fluid interference fringe image (A) and by dividing the tear fluid interference fringe image into 4 divisions (B), 16 divisions (C), 64 divisions (D), and 256 divisions (E). A numerical value represents the color diversity in each region and is measured on a 10-point scale from zero to nine. This figure shows that using a small grid makes it possible to detect a subtle change in a tear fluid interference fringe. If the color diversity is 6 or higher, the tear fluid state is determined to be poor, and such a division is marked by "x".

In a case where one grid is constituted by the entire image, the color diversity scores a moderate value of 4 on the 10-point scale. A resolution increases as a length of sides of the grid is reduced to ½, ¼, ⅛, and 1/16 of the original length, making it possible to grasp the tear fluid state in a small region.

Figure 4A:
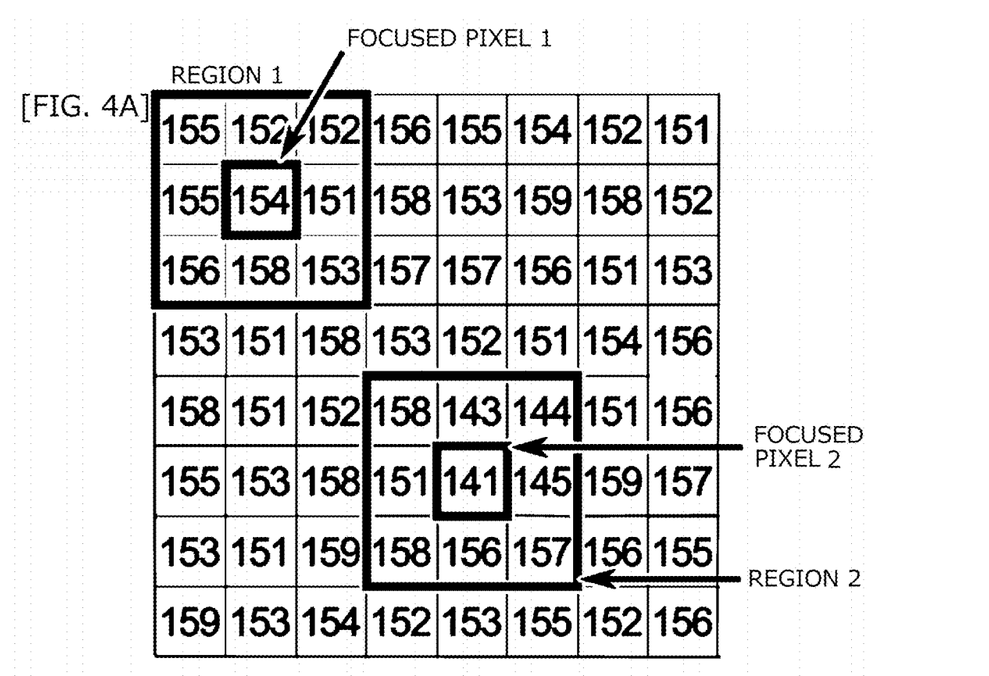
FIG. 4 is a diagram illustrating a method for obtaining the color diversity given to a focused pixel from a standard deviation of luminance in a region including and surrounding the focused pixel without dividing the image into a grid shape for performing an image analysis.
Figure 4B:
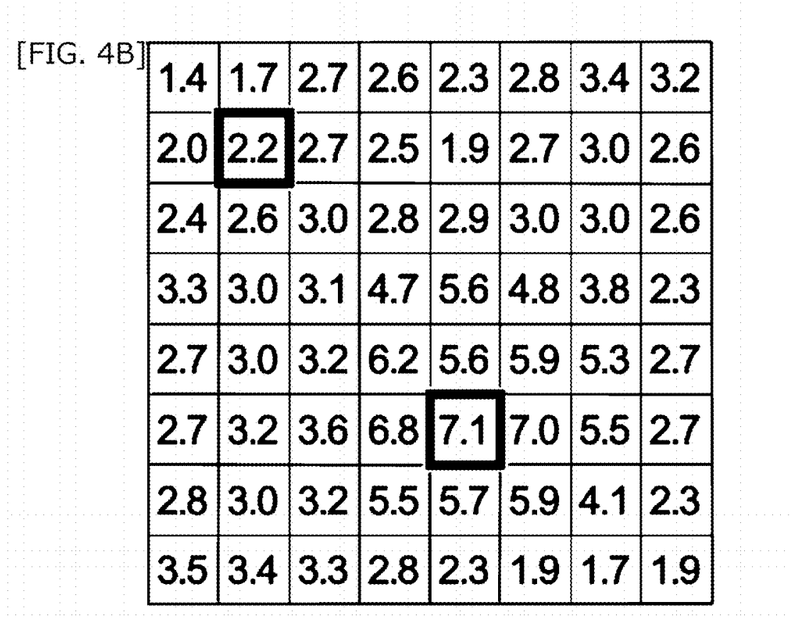

In addition, as shown in FIG. 4, the tear fluid state can be evaluated with a resolution equivalent to that of the original tear fluid interference fringe image without dividing the image into the regions by focusing on an individual pixel or pixel group and obtaining the color diversity of pixels surrounding them. FIG. 4A shows a numerical value of the luminance of each pixel in a tear fluid interference fringe image and FIG. 4B shows a standard deviation that is calculated using a certain pixel and pixels surrounding the certain pixel as a sample.

In the example shown in FIG. 4B, the standard deviation in a focused pixel 1 and a region 1 surrounding the focused pixel 1 is as small as "2.2", while the standard deviation in a focused pixel 2 and a region 2 surrounding the focused pixel 2 is as large as "7.1", thus making it possible to determine that the region 2 has higher color diversity than the region 1 and the tear fluid state is worse in the region 2 than in the region 1. In this manner, the tear fluid state can be grasped and evaluated in each specific position on the cornea.

Example 4

In the method for evaluating the tear fluid state from the color diversity of the interference fringe in Example 3, a video image of the interference fringe was evaluated using the method for evaluating the color diversity of each pixel from colors possessed by surrounding pixels. Specifically, the luminance values were obtained in a total of 25 pixels in a 5×5 matrix having a focused pixel at a center for 3 elements of red, green, and blue (RGB) in each frame image of a tear fluid interference fringe video image and the standard deviations of the luminance values were obtained for 3 RGB elements. Then, an average value of the standard deviations was calculated.

The color diversity of each frame image of the video image was evaluated using the method described above in this manner to successfully capture a process whereby a crack of the tear fluid was developed and grew from a lower eyelid side on the cornea, as shown in FIG. 5.

Figure 5A:
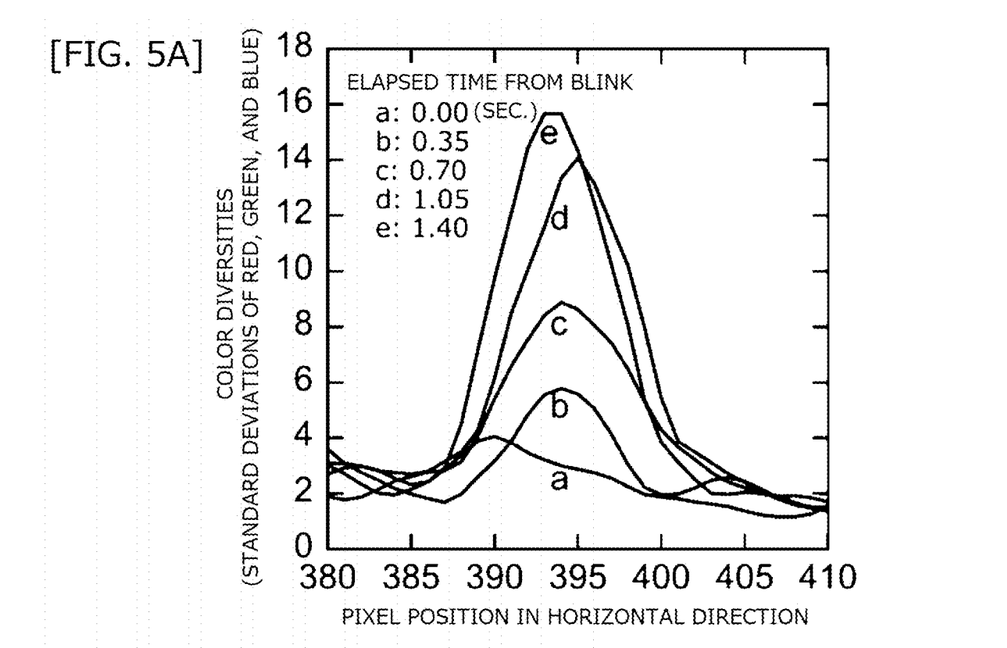
FIG. 5 is a diagram illustrating an example of calculating and dynamically analyzing the color diversity in each frame image using a video image of a tear fluid interference fringe.
Figure 5B:
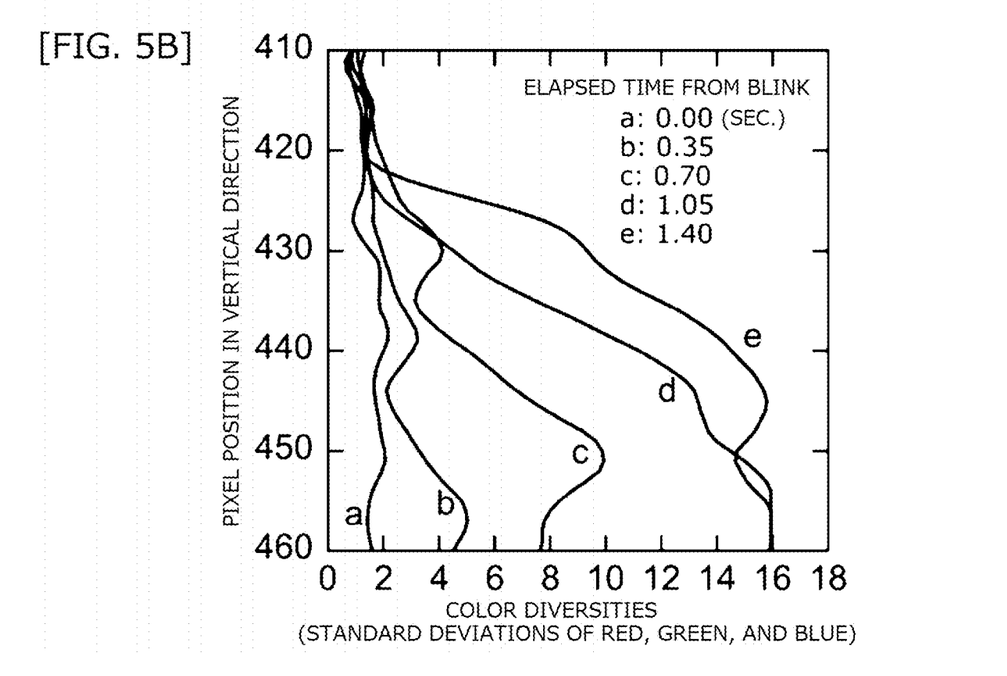

FIG. 5A shows the color diversity in a region including the crack in a lower part of the tear fluid interference fringe image in a horizontal direction, and FIG. 5B shows a time-lapse view of the color diversity in a vertical direction to the horizontal. Various colors emerged near the crack and thus the color diversity of the interference fringe increased. It was found that the color diversity increased in the vertical direction, but not in the horizontal direction, that is, the crack was formed to be recessed upward from the lower eyelid side. In this manner, it becomes possible to analyze a location where the tear fluid collapses on the cornea and a timing of the collapse of the tear fluid, allowing a more detailed diagnosis than the grade determination obtained by observing the entire tear fluid.

Example 5

A method for calculating the standard deviations of red color and blue color as the color diversity of the tear fluid interference fringe obtained by using the methods described in Example 3 and Example 4 and dividing the standard deviation of blue color by the standard deviation of red color was studied. The standard deviation of red color linearly increases up to grade 4, but its numeric value becomes too small in grade 5 in which the tear fluid interference fringe image is dark as a whole. On the other hand, the standard deviation of blue color increases up to grade 5. Thus, the image of grade 5 could be specifically detected by dividing the deviation of blue color by the standard deviation of red color.

While the present invention has been described above, it is to be understood that the present invention is not limited to the above-described examples and may be modified and embodied in various aspects. In the aforementioned description, the tear fluid interference fringe image acquisition device and the tear fluid state evaluation device are described as a separate hardware; however, the tear fluid interference fringe image acquisition device and the tear fluid state evaluation device may be configured as an integrated hardware, and the processing unit, the storing unit, and the like, built in for information processing, may be provided in each of the tear fluid interference fringe image acquisition device and the tear fluid state evaluation device or partially shared by these devices. The tear fluid state evaluation device is only required to have the configuration capable of performing the processing described above to the tear fluid interference fringe image.

Further, the region in which the standard deviation of the luminance is calculated may be the entire image or a small piece (division) obtained by dividing the image into a grid shape. Alternatively, the luminance may be calculated in each pixel and its surrounding region.

A planar (or spatial) distribution of the tear fluid state can be evaluated by appropriately selecting the region from the entire image, each divided region obtained by dividing the entire image into an huge number of regions, or a region surrounding each pixel or a small pixel group, and analyzing and digitizing the color state of the interference fringe per unit of the region.

INDUSTRIAL APPLICABILITY

The present invention can be used as a method for objectively digitalizing the tear fluid state in the diagnosis of the severity of dry eye using the tear fluid interference fringe image without relying on the ability of the observer. In particular, the present invention makes it possible to perform a dynamic analysis of a temporal and spatial transition of the tear fluid, which is difficult to perform by the conventional grade determination by visual inspection. Further, more detailed diagnosis and a treatment adapted to a symptom can be expected by using the method according to the present invention in which the color diversity is evaluated using the variation of the luminance as an index or the histogram of the hue as compared to the conventionally proposed method in which the color information (the luminance value or the hue) of the tear fluid interference fringe image is evaluated as it is.

The invention claimed is:

1. A method for evaluating a tear fluid state by executing the following steps by using a processing unit of a tear fluid state evaluation device comprising:
   a step of acquiring color information in a predetermined region of a tear fluid interference fringe image acquired by an imaging element of a tear fluid interference fringe image acquisition device; and
   a step of calculating a numerical value representing a color diversity from the color information acquired,
   wherein the color information is luminance of one or more color elements of red, green, and blue possessed by a pixel; and
   the numerical value representing the color diversity is a variation of the luminance.

2. The method for evaluating a tear fluid state according to claim 1, wherein the variation of the luminance is a variance of the luminance or a standard deviation of the luminance.

3. The method for evaluating a tear fluid state according to claim 1, wherein:
   the tear fluid interference fringe image includes a plurality of frame images constituting a movie image; and
   the color information in the predetermined region is acquired in each of the frame images and the numerical value representing the color diversity is calculated from the color information acquired.

4. The method for evaluating a tear fluid state according to claim 2, wherein:
the tear fluid interference fringe image includes a plurality of frame images constituting a movie image; and
the color information in the predetermined region is acquired in each of the frame images and the numerical value representing the color diversity is calculated from the color information acquired.

5. A method for evaluating a tear fluid state by using a processing unit of a tear fluid state evaluation device comprising:
a step of acquiring color information in a predetermined region of a tear fluid interference fringe image acquired by an imaging element of a tear fluid interference fringe image acquisition device; and
a step of calculating a numerical value representing a color diversity from the color information acquired, wherein the color information is a hue of the pixel; and
the numerical value representing the color diversity is a ratio between a number of sections in which a number of elements is not empty and a number of sections in which a number of elements is empty, the sections being obtained by dividing the hue into predetermined sections.

6. The method for evaluating a tear fluid state according to claim 5, wherein:
the tear fluid interference fringe image includes a plurality of frame images constituting a movie image; and
the color information in the predetermined region is acquired in each of the frame images and the numerical value representing the color diversity is calculated from the color information acquired.

7. A device configured to evaluate a tear fluid state comprising:
a unit configured to acquire color information in a predetermined region of a tear fluid interference fringe image; and
a calculation unit configured to calculate a numerical value representing a color diversity from the color information acquired,
wherein the color information is luminance of one or more color elements of red, green, and blue possessed by a pixel; and
the numerical value representing the color diversity is a variation of the luminance.

8. A device configured to evaluate a tear fluid state comprising:
a unit configured to acquire color information in a predetermined region of a tear fluid interference fringe image; and
a calculation unit configured to calculate a numerical value representing a color diversity from the color information acquired,
wherein the color information is a hue of the pixel; and
the numerical value representing the color diversity is a ratio between a number of sections in which a number of elements is not empty and a number of sections in which a number of elements is empty, the sections being obtained by dividing the hue into predetermined sections.

* * * * *